United States Patent [19]

Blake

[11] 4,397,867

[45] Aug. 9, 1983

[54] TREATMENT OF ARTHRITIC COMPLAINTS

[75] Inventor: David R. Blake, Bath, England

[73] Assignee: Ciba-Geigy Corporation, Ardsley, N.Y.

[21] Appl. No.: 388,573

[22] Filed: Jun. 15, 1982

[30] Foreign Application Priority Data

Jun. 19, 1981 [GB] United Kingdom ................. 8119006

[51] Int. Cl.³ .............................................. A61K 31/16
[52] U.S. Cl. ................................................... 424/320
[58] Field of Search ......................................... 424/320

[56] References Cited

PUBLICATIONS

Chem. Abst., vol. 94, 167209c (1981).

*Primary Examiner*—Stanley J. Friedman
*Attorney, Agent, or Firm*—Irving N. Feit

[57] ABSTRACT

Rheumatoid arthritic and like diseases involving joint inflammation are treated by administering desferrioxamine in a therapeutically effective dosage over a prolonged period.

7 Claims, No Drawings

TREATMENT OF ARTHRITIC COMPLAINTS

The present invention relates to the treatment of arthritic and like complaints.

The term "arthritic" is used medically to describe the occurrence of inflammation of a joint. Arthritis exists in many forms; rheumatoid arthritis is a chronic form of arthritis where many joints are affected and the inflammation is often such that gross deformity and immobility of the joint may result. Rheumatoid arthritis has, in the past, been treated, for example, with cortisone or with non-steroidal anti-inflammatory drugs. Cortisone is effective in combating inflammation but also carries with its use a high risk of dangerous side effects. Treatment with non-steroidal anti-inflammatory drugs (NSAID's) has often been found not to be as effective as desired to reduce inflammation. The most popular NSAID is aspirin which has to be used in very high doses e.g. 16–18 tablets per day.

It has been previously found that in cases of rheumatoid arthritis there is a low blood plasma iron level but a high amount of iron in the synovial membrane which is stored as ferritin in synovial reticuloendothelial cells.

It has been found that the inflammation of joints mainly in rheumatoid arthritis is exacerbated by the production of free oxygen radicals generated in the presence of catalytic free iron, as opposed to ferritin.

Desferrioxamine is an iron-chelating agent which has long been used in the treatment of iron poisoning and which has also been used extensively in the examination of iron metabolism in many diseases including rheumatoid arthritis. We are not aware, however, that the use of desferrioxamine to reduce the inflammation in the treatment of rheumatoid arthritis has ever been disclosed.

We have surprisingly found that the treatment of rheumatoid arthritis and like diseases by the administration of desferrioxamine over a prolonged period in a suitable dosage gives remarkable reduction in the inflammation of joints. This is all the more surprising when it is realised that small or short term administration of the compound exacerbates the inflammatory condition.

Without wishing to be bound by any theory as to the mechanism of action of desferrioxamine within the body, it is thought that the excess iron stored as ferritin in the reticuloendothelial cells and the free iron in the synovial fluid exist in an equilibrium such that any chelation of the free iron on a short term basis disturbs the iron balance and causes the production of large amounts of free iron from the stored ferritin possibly even overcompensating for the loss of the free iron; the free iron then causes exacerbation of the joint inflammation as indicated above, and it is perhaps for this reason that where desferrioxamine has been used hitherto in studies of iron metabolism that indications have been that it would not be useful for the treatment of rheumatoid arthritis. Prolonged treatment with desferrioxamine is thought, however, to gradually "mop up" the free iron produced and to reduce the amount of free iron available for catalysts giving rise to a reduction in inflammation.

Accordingly, the present invention provides a method of treatment of rheumatoid arthritic and like diseases involving joint inflammation, which comprises administering desferrioxamine in a therapeutically effective dosage over a prolonged period.

The method of the invention may be applied to the treatment of non-specific monoarthritis and any other instances of joint inflammation caused by free iron catalysis. The method of the invention may also be applied to any other complaint which is induced by the occurrence of free iron, for example certain instances of myocardial infarction as recently suggested.

The amount of desferrioxamine administered is suitably a therapeutically effective amount in the range of from 1 to 10 g per day, for example 1 to 5 g per day, suitably 2 to 3 g per day.

The present invention also provides a pharmaceutical preparation suitable for intra-articular administration which comprises desferrioxamine in admixture or conjunction with a pharmaceutically suitable carrier.

The present invention further provides a pharmaceutical preparation in the form of a pack which contains a support member together with a plurality of dosage forms comprising desferrioxamine, preferably enough for 3 weeks' supply.

Suitably the amount of desferrioxamine present in each dosage form in a pack of the invention is in the range of from 1 to 10 g, e.g. in the range of from 1 to 5 g, conveniently 2 to 3 g. The amount of desferrioxamine may be different in each dosage form, for example a pack may comprise a set of dosage forms one containing 1 g of desferrioxamine, another 2 g of desferrioxamine and so on to 5 g, 7 g or 10 g of desferrioxamine. The desferrioxamine is suitably present in lyophilised powder form as desferrioxamine mesylate but may be in a liposome formulation.

Desferrioxamine may be administered by any one of several routes. Administration intravenously, intraperitoneally, subcutaneously, intra-muscularly or intra-articularly by infusion solution are all suitable routes, intra-articular and subcutaneous infusion being preferred. Administration by infusion solution may be by continuous pump administration or administration in divided doses, i.e. twice or three times daily, daily, weekly or monthly. The active substance may be present in the infusion solution prior to the start of the administration or may be injected in as a "bolus" concentrate. Other routes of administration possible are via the skin or by the use of a liposome formulation.

Administration via the skin may be by the transdermal "delivery system" (Alza Corporation) where medication externally applied by means of a special applicator reaches the affected joint by absorption through the skin. Direct topical administration may occur from once to four times daily by means of an ointment or cream containing desferrioxamine.

Preparations containing desferrioxamine may in addition contain the usual carriers, excipients and auxiliaries. In infusion solutions, for example, pH-regulating substances, e.g. sodium phosphate and substances imparting isotonicity to the solutions, e.g. sodium chloride, may be present.

The period of administration of desferrioxamine will vary depending on the severity of the disease, but is usually at least 5 days. In chronic cases the administration may occur initially over a period of 3 weeks to a month with the treatment being repeated at 3, 6 or 12 month intervals or sooner if chronic inflammation occurs or recurs. In instances of subcutaneous administration by infusion solution, it has been found satisfactory for the initial 3 week treatment to consist of continuous administration over several hours daily for 5 consecutive days, followed by no administration for 2 days and then repeat treatment for the following 5 days and so on.

The above methods of administration are acceptable methods for introducing desferrioxamine into the body but cannot ensure that all of the active substance reaches the site of the free iron and ferritin stores in the reticuloendothelial stores. Also the most useful preparations, the infusion solutions, have to be made up shortly before use from lyophilised desferrioxamine powder because aqueous desferrioxamine solution is unstable over periods of longer than a week.

The present invention also provides a method for the treatment of rheumatoid arthritis, wherein a pharmaceutical preparation comprising desferrioxamine as a liposome formulation is administered to the patient orally or parenterally. Liposomes are lipid vesicles of varying sizes which encapsulate an active ingredient. The lipid walls may comprise one or more lipid bi-layers. Suitable lipids are phospholipids; they may be used in pure form or in combination with other suitable substances. Desferrioxamine in aqueous solution may be incorporated into liposomes which have an avidity for the reticuloendothelial cells without apparent loss of stability. With such a formulation the desferrioxamine may "home in" on the reticuloendothelial cells and it is believed that such formulations will enable smaller amounts of desferrioxamine to be administered for the same anti-inflammatory effect because the active substance is retained in the liposomes until the site of action is reached. Liposomes may be administered by enteral or parenteral means, preferably by intra-articular injection or by oral administration. Suitably each liposome formulation may contain in the range of 0.1 to 12.5 mg of desferrioxamine.

Administration of desferrioxamine when entrapped in red cell ghosts is also possible to counter inflammation.

Desferrioxamine has been found to give a significant reduction in joint inflammation in patients suffering from rheumatoid arthritis without any apparent side-effects. It has also been found to give such results when used in conjunction with non-steroidal anti-inflammatory drugs without any apparent undesirable interactions. Desferrioxamine may thus be used as a replacement for or as a supplement to the non-steroidal anti-inflammatory drugs already used.

The following Examples illustrate the invention.

Desferrioxamine Preparations

I. Infusion Solutions
(a) The contents of an ampoule containing 500 mg of lyophilised desferrioxamine (commercially available under the trade name Desferal in the form of lyophilised desferrioxamine mesylate) were completely dissolved in 2-3 ml of Water for Injection BP and then made up to the required amount with a suitable infusion solution. An infusion solution containing 1 g of desferrioxamine was similarly prepared using 2 ampoules as above. Also solutions containing 2 g (using 4 ampoules), 3 g (using 6 ampoules), 5 g (using 10 ampoules), 7 g (using 14 ampoules) and 10 g (using 20 ampoules) of desferrioxamine. Suitable infusion solutions are normal saline, dextrose, dextrose saline, blood and Ringers Lactate solution.
(b) 1 g of desferrioxamine was dissolved in 10 ml of Water for Injection BP to give a 10% solution of desferrioxamine. Sufficient sodium chloride to render the solution isotonic was added. Such a solution may be diluted with suitable infusion solutions (as mentioned above) or may be used as a concentrated or "bolus" solution.

II. Ointment

An ointment containing 5% by weight of desferrioxamine based on 0.4% of cetyl alcohol, 4.6% of wool fat, 65% of white soft paraffin and 30% of liquid paraffin, was prepared by known procedure comprising heating the cetyl alcohol, wool fat, white soft paraffin and liquid paraffin together and incorporating the desferrioxamine.

III. Liposomes

The liposomes were prepared with a mixture of dipalmitoyl phosphatidylcholine, cholesterol and stearylamine, in a molar ratio of 3.6:2.3:1 respectively, dissolved in chloroform. This mixture was dried in a round bottom flask in a rotary evaporator. The flask was placed in a 37° C. water bath and 1 ml of a 10-12% aqueous solution of desferrioxamine mesylate was slowly added to the flask with immediate and constant stirring with a magnetic stirrer. The resultant suspension of liposomes containing desferrioxamine was centrifuged at 2000 rpm for 5 minutes. The supernatant was carefully pipetted off and the liposome pellet was suspended in normal saline. The centrifugation and resuspension procedure was repeated five times to ensure the complete removal of nonencapsulated desferrioxamine solution. For injection, the liposomes are to be resuspended in saline.

Other liposome preparations were prepared by similar known methods using the lipid mixtures given below. The abbreviations noted designate the following compounds:
CH=cholesterol
DP=dicetyl phosphate
DMPC=dimyristoyl phosphatidylcholine
DOPC=dioleoyl phosphatidylchloline
DPPC=dipalmitoyl phosphatidylcholine
PA=phosphatidic acid
PC=egg phosphatidylcholine
PCA=egg phosphatidic acid
PS=phosphatidylserine
SA=stearylamine Unless specifically stated, the solvent used for the lipoid mixture was chloroform.
1. 6 mg DPPC and 3 mg PCA in 1.25 ml chloroform.
2. 22.5 mg PC and CH in 10-15 ml chloroform
PC and PA in a molar ratio of 7:1
4. PC, CH and PA in a molar ratio of 7:2:1
5. PC, CH and SA in a molar ratio of 7:2:1
6. PC, CH and DP in a molar ratio of 7:2:1
7. PC, CH and PA in a molar ratio of 7:5:1
8. PC, CH and SA in a molar ratio of 7:5:1
9. DOPC, CH and PA in a molar ratio of 7:5:1
10 DMPC, CH and PA in a molar ratio of 7:5:1
11. PC and CH in a molar ratio of 8:2
12. PC and CH in a molar ratio of 9:2
13. DPPC, CH and PA in a molar ratio of 7:2:1
14. PC, CH and PS in a molar ratio of 7:2:1

The size of the liposomes was varied in certain cases from multilamellar liposomes to unilamellar liposomes by ultrasonication.

Animal Tests

Inflammation of joints was induced by various recognised methods as indicated below and the effects of administered desferrioxamine were studied.

I. Induction by ureates

Crystal ureate was used to induce footpad swelling in rats. 1 mg, 10 mg, 30 mg and 60 mg doses of desferrioxamine per kg were administered, each to different rats, and the footpad swelling was measured after 2 and 24 hours.

The rats which had received the 1 mg/kg and 10 mg/kg doses exhibited significantly increased swelling of the affected footpad whilst the higher doses showed a marked anti-inflammatory effect with reduced swelling.

II. Induction by carrageenan

Carrageenan was used to induce footpad swelling in rats. Two doses of desferrioxamine were studied: 1 mg/kg and 60 mg/kg. The 1 kg/kg dose exhibited no effect on the footpad swelling whilst the 60 mg/kg dose significantly reduced the footpad swelling.

III. Induction by Bovine Gamma Globulin (BGG)

The Glynn-Dumonde model of adjuvant arthritis was followed which involves the injection of BGG in Freunds complete adjuvant to instigate inflammation followed by a second injection of BGG after 10 days to maintain the induced swelling.

50 mg/kg of desferrioxamine were administered to one group of rats at the time of the second injection and the same amount was administered to a second group of rats on days 7 to 14.

The dose on day 10 exacerbated the arthritis whilst that on days 7 to 14 exhibited a reduction in the inflammation of the adjuvant arthritis each compared to a control group of rats to which no desferrioxamine was administered.

IV. Induction by mycobacteria

Adjuvant arthritis was induced by mycobacteria. 30 mg/kg of desferrioxamine were administered to a first group of rats on each of the first 5 consecutive days after induction. A reduction in the primary lesions over a group of control rats was noted. 30 mg/kg of desferrioxamine were administered to a second set of rats on each of the 15th to 19th days after induction and note was taken of the effect on secondary lesions. The second set of rats had reduced secondary lesions over the control rats and also over the first set of rats which now exhibited worse secondary lesions than the control rats.

Tests on Humans

1. One patient with non-specific monoarthritis of the knee received 5 daily injections of desferrioxamine intra-articularly after synovial fluid aspiration. Doses of desferrioxamine were increased daily until on days 4 and 5 the patient received 1 g of desferrioxamine (injected over 1 hr). The total dose of desferrioxamine injected was 3.5 g.

Results (a) No local or systemic side effects were observed.
(b) There was a noticeable reduction of the swelling of the knee which continued for 3 months after the injection (longer relief than had previously been experienced).
(c) Synovial fluid showed reduction of catalytic iron and thiobarbituric acid reactivity.
(d) Synovial fluid ferritin levels were reduced, but no changes were found in the serum.
(e) In 3 hours after injection there was marked leucocytosis in the synovial fluid.

2. Nine patients with active rheumatoid arthritis received 1 g of desferrioxamine daily for 3 weeks (treatment on 5 days a week only) by subcutaneous infusion over 7 to 8 hours. All patients were admitted to the hospital for the time of the trial. Treatment with non-steroidal anti-inflammatory drugs was continued throughout the trial.

The following clinical and laboratory parameters were evaluated at weeks 1 and 3:

Ritchie index, morning stiffness, grip strength, VAS pain scores, FBC, ESR, rheumatoid factor, immunoglobulins, iron, thiobarbituric acid reactivity.

Results

No changes in the laboratory parameters were found; however, thiobarbituric acid reactivity was reduced in some patients studied. Clinical indices of disease activity showed improvement at week 3 (8 patients out of 9) despite, after 1 week of treatment, 8 out of 9 patients having experienced flare-up of their arthritis and 1 patient having developed vasculitis (this cleared after the 3 weeks of treatment).

No side effects were reported.

I claim:

1. A method for the treatment of rheumatoid arthritic and like diseases involving joint inflammation, which comprises administering to patents in need of such administration desferrioxamine in a therapeutically effective dosage over a prolonged period sufficient to reduce joint inflammation.

2. A method as claimed in claim 1 in which the amount of desferrioxamine administered is from 1 to 10 g per day.

3. A method as claimed in claim 2 in which the amount of desferrioxamine administered is from 2 to 3 g per day.

4. A method as claimed in any one of claims 1 to 5 in which the period of administration is at least 15 days.

5. A method as claimed in claim 4 in which the period of administration is at least 3 weeks.

6. A method as claimed in any one of claims 1 to 5 in which the desferrioxamine is administered intravenously, intraperitoneally, subcutaneously, intramuscularly, intraarticularly or transdermally.

7. A method as claimed in any one of claims 1 to 5 in which the desferrioxamine is administered orally or parenterally in the form f a liposome formulation wherein the desferrioxamine is encapsulated in lipoid vesicles.

* * * * *